(12) United States Patent
Galipeau et al.

(10) Patent No.: US 6,327,890 B1
(45) Date of Patent: Dec. 11, 2001

(54) HIGH PRECISION ULTRASONIC CHILLED SURFACE DEW POINT HYGROMETRY

(76) Inventors: David W. Galipeau, 1322 Fourth St.; Russell D. Mileham, 1457 6th St., both of Brookings, SD (US) 57006

( * ) Notice: Subject to any disclaimer, the term of this patent is extended or adjusted under 35 U.S.C. 154(b) by 0 days.

(21) Appl. No.: 09/377,191

(22) Filed: Aug. 19, 1999

(51) Int. Cl.[7] .................................................. A61B 10/00
(52) U.S. Cl. ...................... 73/24.06; 73/29.02; 73/29.05; 73/31.06; 73/61.79; 310/313 B; 310/313 R
(58) Field of Search ................................ 73/24.01, 24.06, 73/31.06, 32 A, 54.41, 599, 61.79, 29.02, 29.05; 310/313 D, 313 B, 313 R

(56) References Cited

U.S. PATENT DOCUMENTS

| | | | |
|---|---|---|---|
| 4,691,714 | * | 9/1987 | Wong et al. ............................ 73/570 |
| 5,003,822 | * | 4/1991 | Joshi .................................. 73/204.23 |
| 5,364,185 | * | 11/1994 | VanZandt et al. ...................... 374/28 |
| 5,918,258 | * | 6/1999 | Bowers ............................... 73/24.06 |
| 6,122,954 | * | 9/2000 | Bowers ............................... 73/24.06 |

* cited by examiner

Primary Examiner—Hezron Williams
Assistant Examiner—Rose M. Miller

(57) ABSTRACT

A improvement for high precision ultrasonic chilled surface dew point hygrometry for measuring the density of condensation and the temperature at the same location on the surface of the sensor. The improvement for high precision ultrasonic chilled surface dew point hygrometry includes a piezoelectric substrate, and further having a conventional thermoelectric cooler connected thereto and a plurality of spaced heat sinks conventionally depending from the surface. Conventional acoustic devices are used to propagate surface acoustic waves and surface skimming bulk waves across the surface of the sensor. A series of the surface acoustic waves is used to measure the density of the condensation at a particular location on the surface of the sensor. A conventional wave detection device such as a phase detector detects the waves as to their velocity and amplitude and passes this information onto a computer microprocessor which is programmed to measure and control the density of the condensate located along the path of the waves across the surface of the sensor. A series of surface skimming bulk waves are preferably propagated across the surface of the sensor at generally an angle to the surface acoustic waves so as to measure temperature of the surface of the sensor without interfering with the surface acoustic waves. Other temperature measuring techniques can also be used, one of which includes using a conventional integrated resistive temperature device disposed in a nonobvious configuration so as not to interfere with the surface acoustic waves on the surface of the sensor.

20 Claims, 8 Drawing Sheets

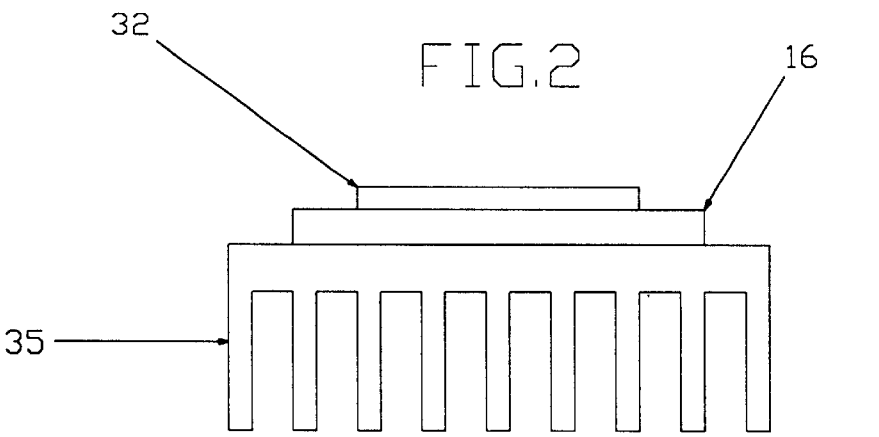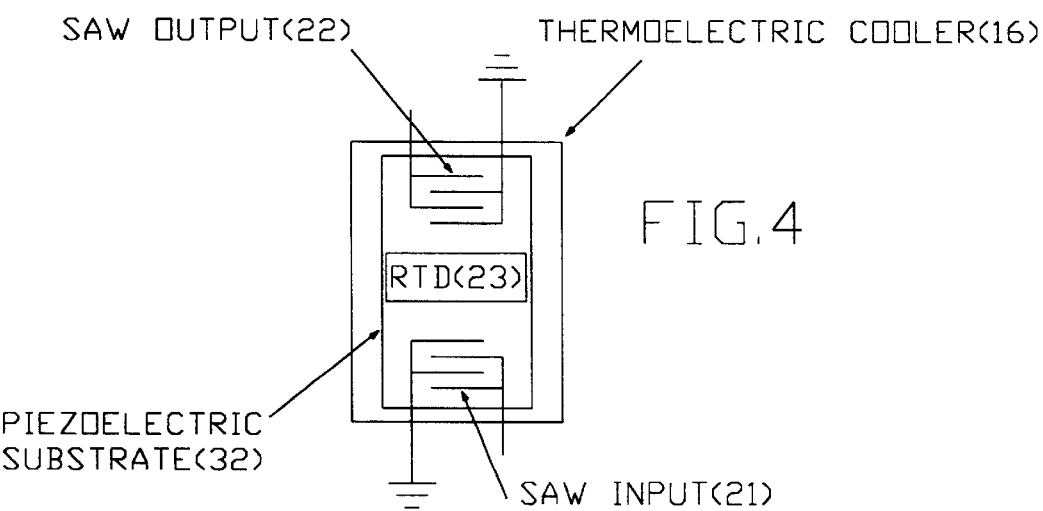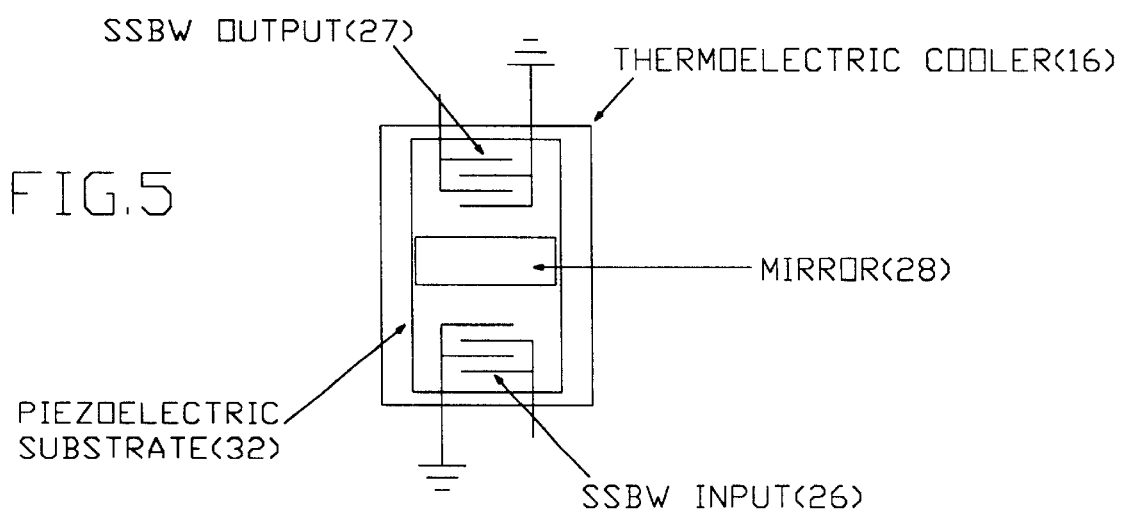

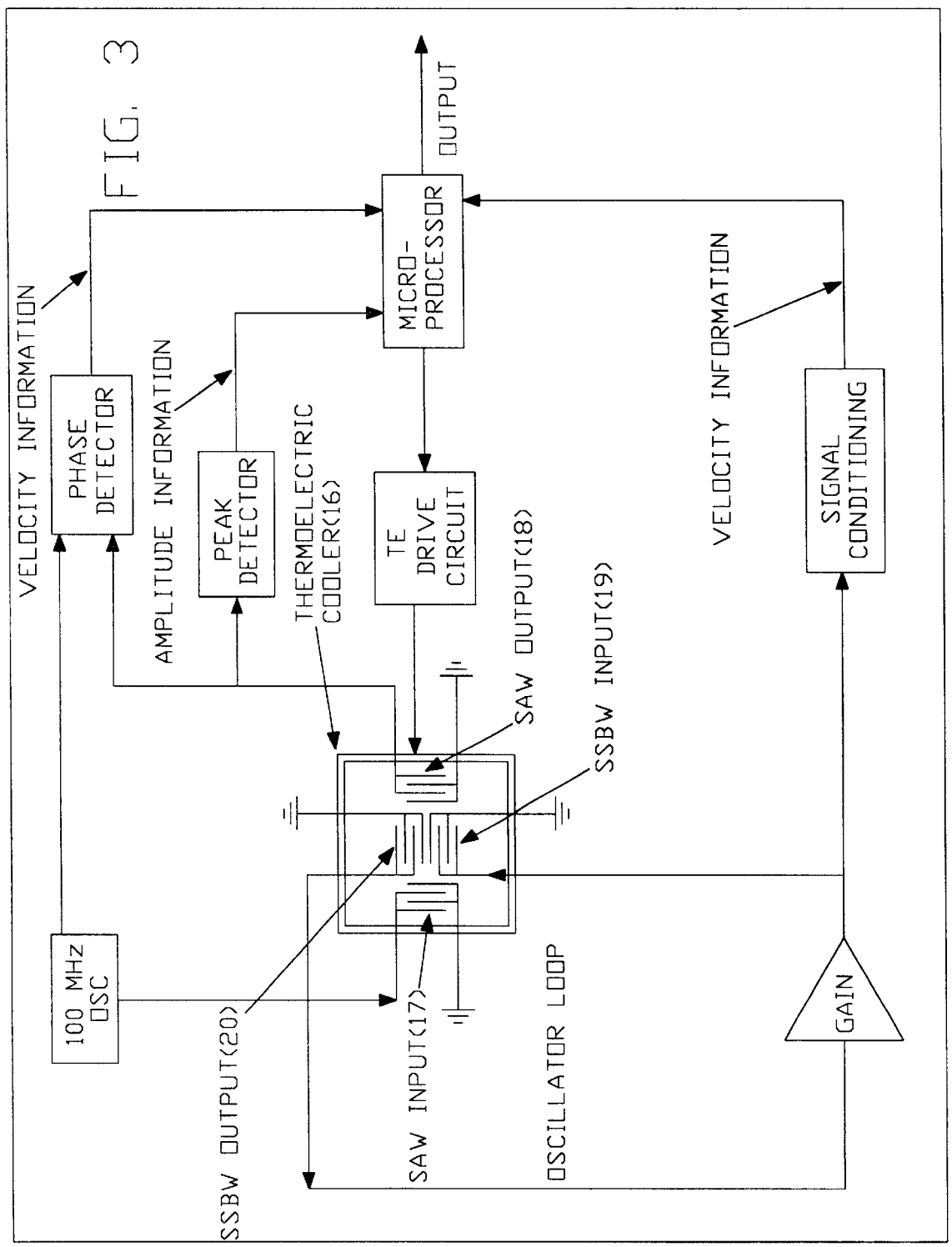

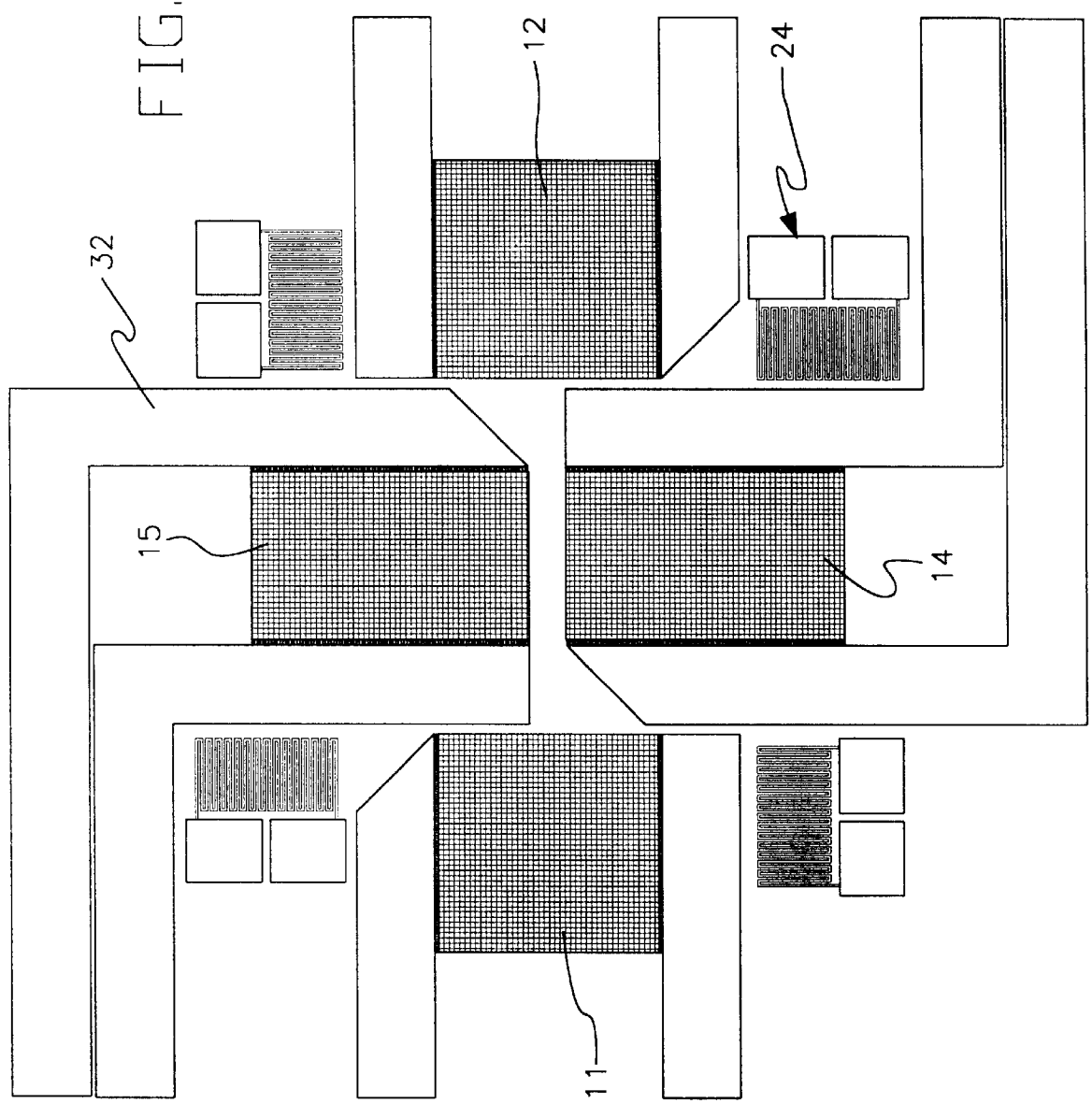

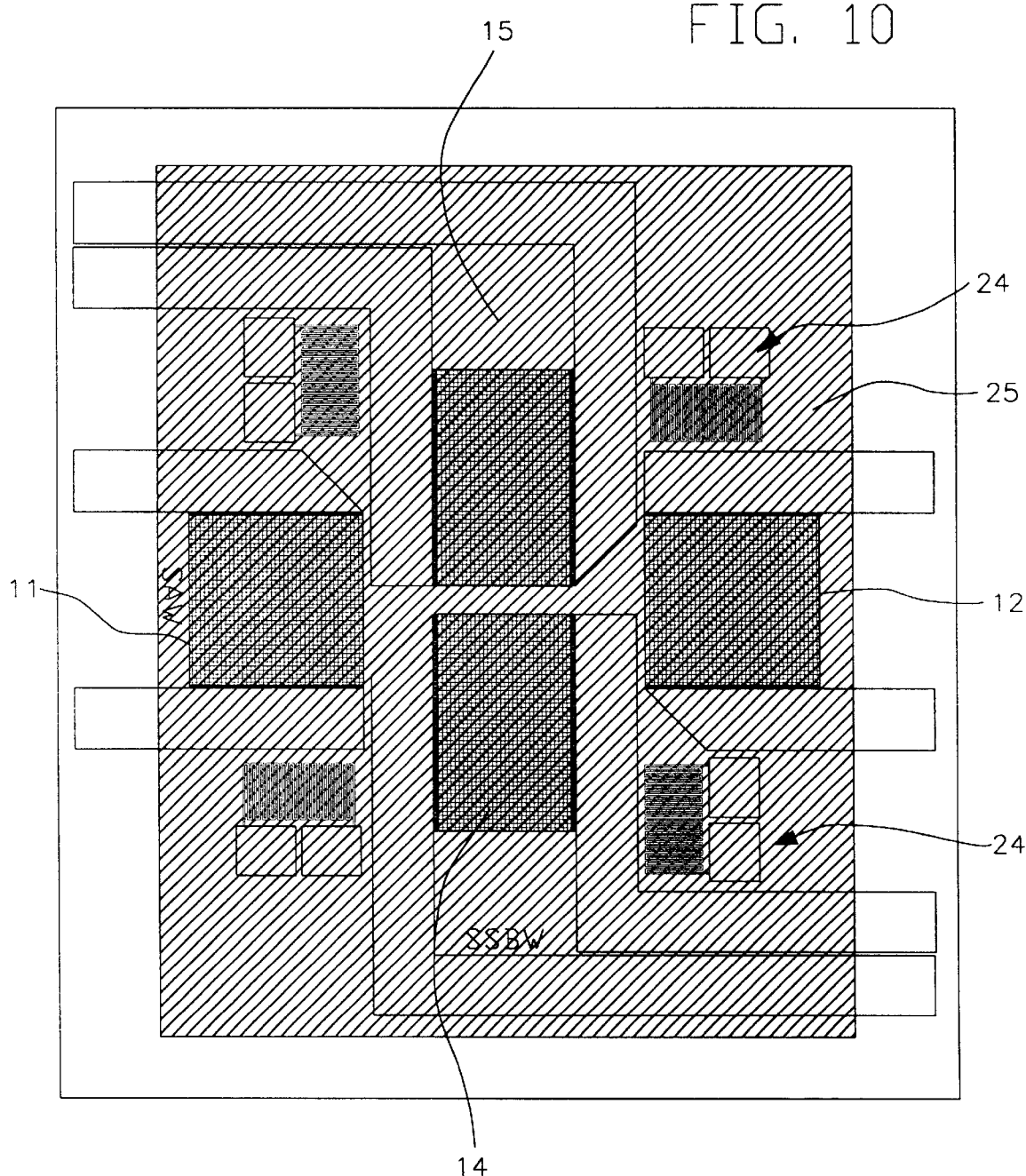

HIGH PRECISION ULTRASONIC CHILLED SURFACE DEW POINT HYGROMETRY

BACKGROUND OF THE INVENTION

1. Field of the Invention

The present invention relates to system and method used to measure the condensate and the temperature at the same location on a sensor and more particularly pertains to a new improvement for high precision ultrasonic chilled surface dew point hygrometry for measuring the density of the condensation and the temperature at the same location on the surface of the sensor. This invention was made with government support under DMI9531504 awarded by the National Science Foundation and the government has certain rights in this invention.

2. Description of the Prior Art

The use of a system and method used to measure the condensate and the temperature at the same location on a sensor is known in the prior art. More specifically, system and method used to measure the condensate and the temperature at the same location on a sensor heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,739,416; U.S. Pat. No. 4,876,889; U.S. Pat. No. 4,088,969; U.S. Pat. No. 4,345,455; U.S. Pat. No. 5,139,344; and U.S. Pat. No. 4,948,263.

Chilled mirror hygrometry is the most widely used form of chilled surface dew point measurements. There are several instruments available that use this technique combined with continuous control of the dew layer such as the Edgetech (formerly EG&G) series 2000 Models and General Eastern Models Hygro-M1 and M2. These instruments provide continuous dew point measurements by using optical reflection to detect and control the condensate while using a resistive temperature device (RTD) to measure the temperature. They are limited to an accuracy and resolution of +/−0.2 C, are sensitive to mirror contamination, become unstable as the dew deposit freezes, and cannot determine the phase of the deposit. Protometer PLC markets a chilled mirror instrument, the System 996, where the mirror is alternately cycled between dry and wet, and the dew point temperature is measured as the mirror enters the wet phase. This cycling reduces contamination effects and avoids the frost point transition since the dew does not have time to freeze in the temperature range that the instrument operates, but with the trade-offs of reduced accuracy and non-continuous measurements.

Surface acoustic waves (SAWs) to detect condensation and control condensation density on the surface of the sensor were first described in U.S. Pat. No. 4,378,168 issued to Kuisma et al. This design uses SAW attenuation in a single sensor (delay line) configuration. It further uses a thermo-element attached to the sensor surface to measure the surface temperature. The invention described in U.S. Pat. No. 5,364,185 issued to VanZandt et al. claims to vary from current chilled mirror instruments in two respects: 1) It uses interdigital transducers (IDTs) to detect water vapor using changes in capacitance or the resonant frequency of a surface acoustic wave resonator; and 2) a parametric approach of dew point detection in which a change in transducer output is measured as a function of a specific thermodynamic quantity. Specifically they use a peak in the second derivative of the moisture signal versus temperature to indicate the dew point which they suggest is relatively immune to surface contamination. The temperature can be measured with a temperature sensor that is located alongside of the SAW resonator. This system can also be less sensitive to surface contamination than optical techniques. SAWs have been used by other investigators such as Hauden et al. (see D. flauden, G. Jaillet and R. Coquerel, "Temperature Sensor Using SAW Delay Line," IEEE Ultrasonics Symposium, 1981, p. 148–151) and Neumeister et al. (see J. Neumeister, R. Thum and E. Luder, "A SAW Delay-line Oscillator as a High-resolution Temperature Sensor, Sensors and Actuators A21A23 (1990) 670–672) to measure temperature, while Mingfang and Haiguo (see L. Mingfang and L. Haiguo, "SAW temperature and humidity sensor with high resolution," Sensors and Actuators B, 12 (1993) 53–56) used a dual delay line SAW sensor to measure both temperature and humidity by coating one delay line with a polymer. Hoummady et al. (see M. Hoummady et al., "Surface acoustic wave (SAW) dew point sensor: application to dew point hygrometry," Sensors and Actuators B, 26–27(1995) 315–317) used SAWs to provide non-continuous dew point measurements by cooling a single delay line SAW device until dew formed and then measuring the dew point temperature as a discontinuity in the frequency versus temperature curve of the SAW device. However, no one has developed a SAW or other acoustic sensor method that can measure temperature while continuously maintaining a constant condensation density using a dual sensor approach.

The most significant limitations of this current art are some or all of the following: 1) temperature measurement inaccuracy due to temperature gradients between the condensate location and the RTD, and self heating of the RTD; 2) limited resolution; 3) instability during the frost point transition; 4) inability to determine the phase of the condensate; 5) non-continuous measurements.

While these devices fulfill their respective, particular objectives and requirements, the aforementioned patents do not disclose a new improvement for high precision ultrasonic chilled surface dew point hygrometry. The inventive device includes a piezoelectric sensor having a surface comprising a piezoelectric substrate, and further having a conventional thermoelectric cooler connected thereto and a plurality of spaced heat sinks conventionally depending from the surface. Conventional acoustic devices are used to propagate surface waves across the surface of the sensor. A series of surface acoustic waves are used to measure the density of the condensation at a particular location on the surface of the sensor. A conventional wave detection device such as a phase detector detects the waves as to its velocity and amplitude and passes this information onto a computer microprocessor which is programmed to measure and control the density of the condensate located along the path of the waves across the surface of the sensor. A series of surface skimming bulk waves are preferably propagated across the surface of the sensor at generally an angle to the surface acoustic waves so as to measure temperature of the surface of the sensor without interfering with the surface acoustic waves. Other temperature measuring techniques can also be used, one of which includes using a conventional integrated resistive temperature device disposed in a nonobvious configuration so as to not to interfere with the surface acoustic waves on the surface of the sensor.

In these respects, the improvement for high precision ultrasonic chilled surface dew point hygrometry according to the present invention substantially departs from the conventional concepts and designs of the prior art, and in so doing provides an apparatus primarily developed for the measuring the density of condensation and the temperature at the same location on the surface of the sensor.

SUMMARY OF THE INVENTION

In view of the foregoing disadvantages inherent in the known types of system and method used to measure the condensate and the temperature near the same location on a sensor now present in the prior art, the present invention provides a new improvement for high precision ultrasonic chilled surface dew point hygrometry construction wherein the same can be utilized for measuring the density of the condensation and the temperature at the same location on the surface of the sensor.

The general purpose of the present invention, which will be described subsequently in greater detail, is to provide a new improvement for high precision ultrasonic chilled surface dew point hygrometry apparatus and method which has many of the advantages of the system and method used to measure the condensate and the temperature at the same location on a sensor mentioned heretofore and many novel features that result in a new improvement for high precision ultrasonic chilled surface dew point hygrometry which is not anticipated, rendered obvious, suggested, or even implied by any of the prior art system and method used to measure the condensate and the temperature at the same location on a sensor, either alone or in any combination thereof.

To attain this, the present invention generally comprises a piezoelectric sensor having a surface comprising a piezoelectric substrate, and further having a conventional thermoelectric cooler connected thereto and a plurality of spaced heat sinks conventionally depending from the surface. Conventional acoustic devices are used to propagate surface waves across the surface of the sensor. A series of surface acoustic waves are used to measure the density of the condensation at a particular location on the surface of the sensor. A conventional wave detection device such as a phase detector detects the waves as to their velocity and amplitude and passes this information onto a computer microprocessor which is programmed to measure and control the density of the condensate located along the path of the waves across the surface of the sensor. A series of surface skimming bulk waves are preferably propagated across the surface of the sensor at generally an angle to the surface acoustic waves for measuring temperature of the surface of the sensor. Other temperature measuring techniques can also be used, one of which includes using a conventional integrated resistive temperature device disposed in a nonobvious configuration so as not to interfere with the surface acoustic waves while minimizing temperature gradients on the surface of the sensor.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new improvement for high precision ultrasonic chilled surface dew point hygrometry apparatus and method which has many of the advantages of the system and method used to measure the condensate and the temperature at or near the same location on a sensor mentioned heretofore and many novel features that result in a new improvement for high precision ultrasonic chilled surface dew point hygrometry which is not anticipated, rendered obvious, suggested, or even implied by any of the prior art system and method used to measure the condensate and the temperature at or near the same location on a sensor, either alone or in any combination thereof.

It is another object of the present invention to provide a new improvement for high precision ultrasonic chilled surface dew point hygrometry which may be easily and efficiently manufactured and marketed.

It is a further object of the present invention to provide a new improvement for high precision ultrasonic chilled surface dew point hygrometry which is of a durable and reliable construction.

An even further object of the present invention is to provide a new improvement for high precision ultrasonic chilled surface dew point hygrometry which is susceptible of a low cost of manufacture with regard to both materials and labor, and which accordingly is then susceptible of low prices of sale to the consuming public, thereby making such improvement for high precision ultrasonic chilled surface dew point hygrometry economically available to the buying public.

Still yet another object of the present invention is to provide a new improvement for high precision ultrasonic chilled surface dew point hygrometry which provides in the apparatuses and methods of the prior art some of the advantages thereof, while simultaneously overcoming some of the disadvantages normally associated therewith.

Still another object of the present invention is to provide a new improvement for high precision ultrasonic chilled surface dew point hygrometry for measuring the density of condensation and the temperature at the same location on the surface of the sensor.

Yet another object of the present invention is to provide a new improvement for high precision ultrasonic chilled surface dew point hygrometry which includes a piezoelectric surface, a thermoelectric cooler connected thereto, and a plurality of spaced heat sink members depending therefrom, and further includes acoustic wave devices, integrated resistive temperature devices and reflective devices.

Still yet another object of the present invention is to provide a new improvement for high precision ultrasonic chilled surface dew point hygrometry that provides better measurement accuracy and resolution.

Even still another object of the present invention is to provide a new improvement for high precision ultrasonic chilled surface dew point hygrometry that improves the measurement stability during the frost point transition and the ability to determine the state of the condensate.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a side view of the sensor for the present invention.

FIG. 3 is another schematic diagram of the second embodiment of the present invention.

FIG. 4 is a schematic diagram of a third embodiment of the present invention.

FIG. 5 is a schematic diagram of a fourth embodiment of the present invention.

FIG. 6 is a top plan view of the second embodiment showing in particular the arrangement of the resistive integrated temperature devices relative to the sensor.

FIG. 10 is a top plan view of the embodiment shown in FIG. 6 showing the sensing film/membrane in relationship to the arrangement of the integrated resistive temperature devices relative to the sensor.

DESCRIPTION OF THE PREFERRED EMBODIMENT

Figure 1:
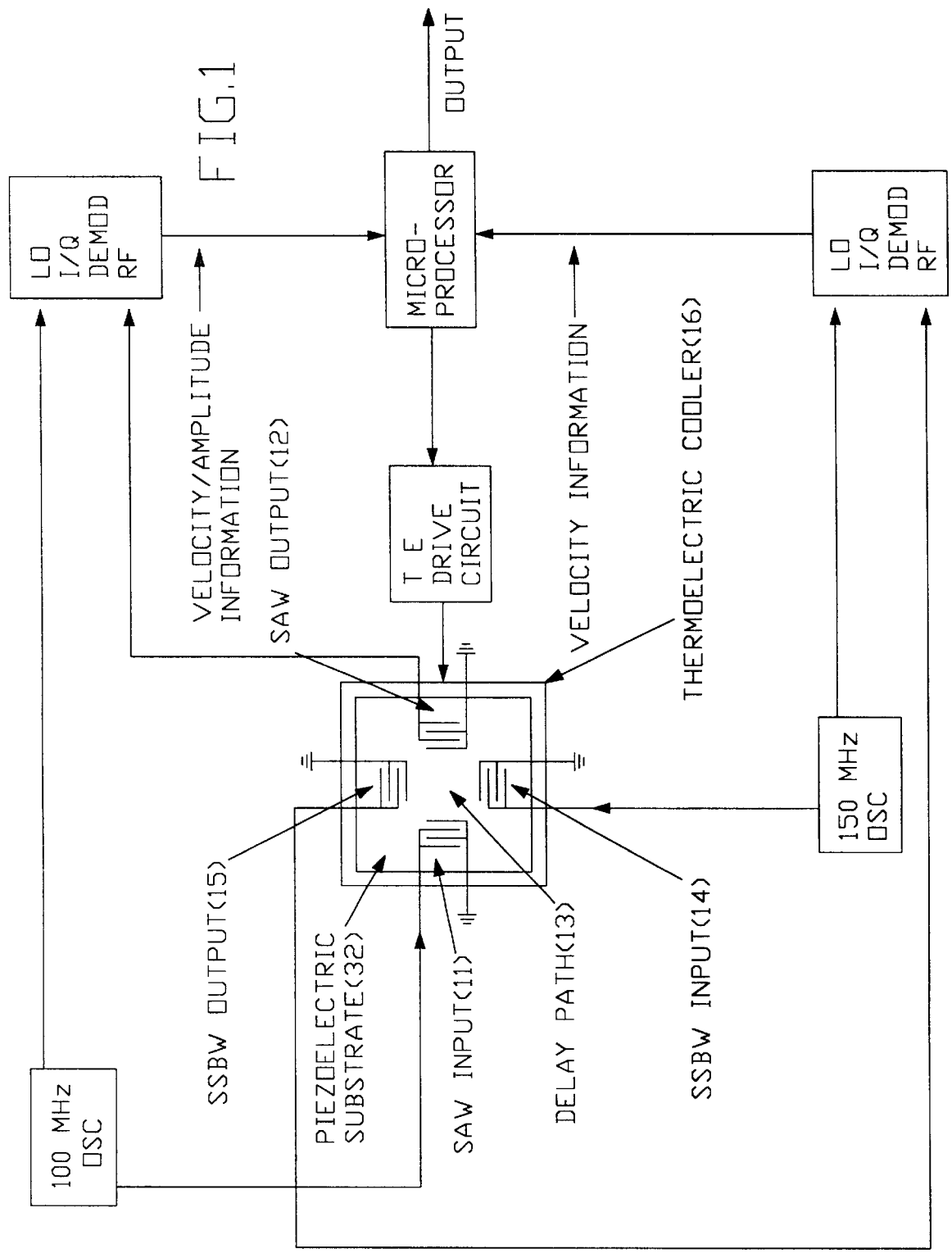
FIG. 1 is a schematic diagram of a first embodiment of a new improvement for high precision ultrasonic chilled surface dew point hygrometry according to the present invention.
Figure 7:
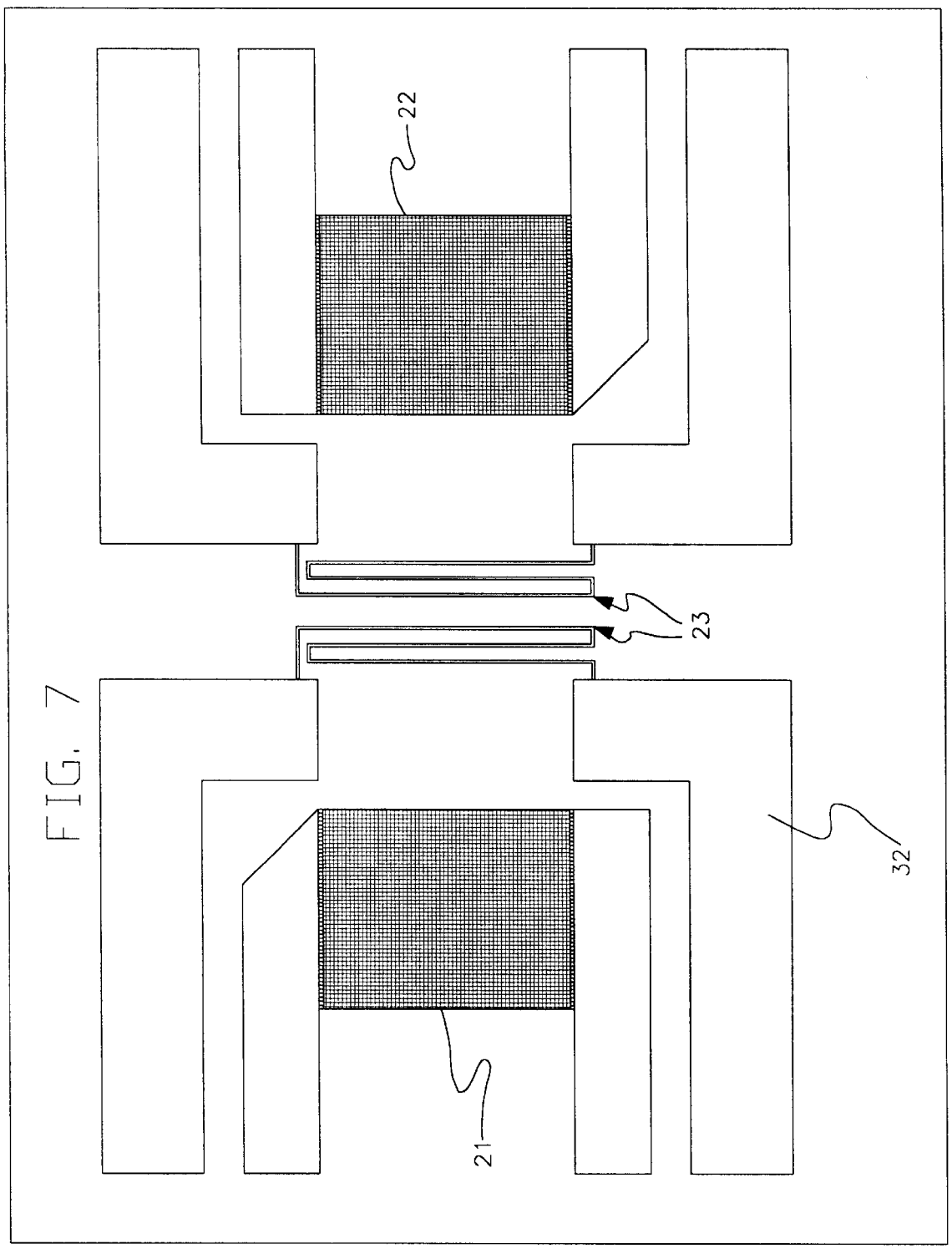
FIG. 7 is a top plan view of the third embodiment showing in particular the arrangement of the resistive integrated temperature devices relative to the sensor.
Figure 8:
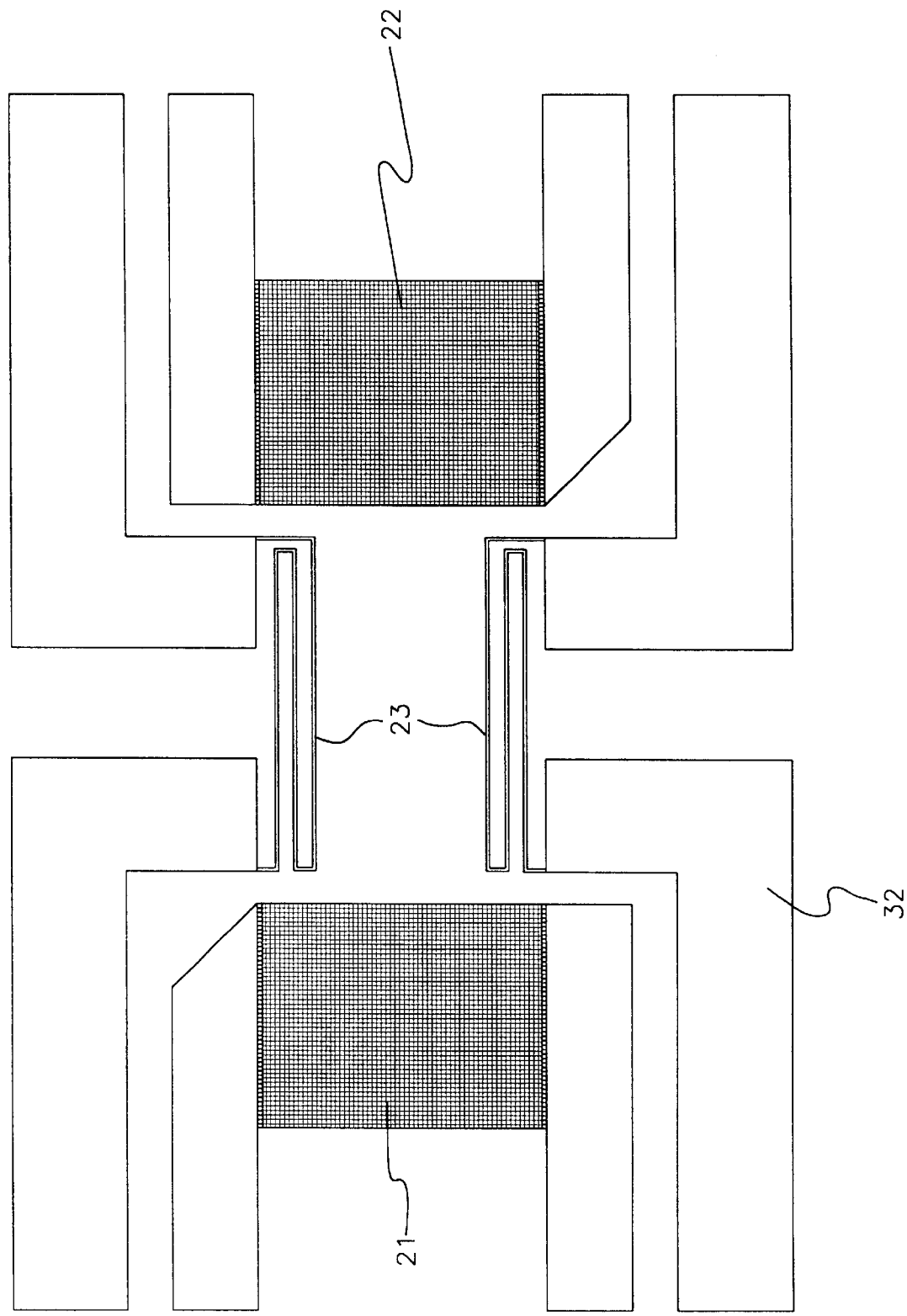
FIG. 8 is a top plan view of the third embodiment showing in particular another arrangement of the integrated resistive temperature devices relative to the sensor.

With reference now to the drawings, and in particular to FIGS. 1 through 8 thereof, a new improvement for high precision ultrasonic chilled surface dew point hygrometry embodying the principles and concepts of the present invention and generally designated by the reference numeral 10 will be described.

As best illustrated in FIGS. 1 through 8, the improvement for high precision ultrasonic chilled surface dew point hygrometry 10 generally comprises a piezoelectric sensor having a surface comprising a piezoelectric substrate, and further having a conventional thermoelectric cooler connected to the surface and a plurality of spaced heat sinks depending from the surface. The accuracy and resolution of the dew point measurements will be improved by combining the high sensitivity of acoustic waves to the condensate, with novel designs which locate the temperature sensor at the same physical location as the condensate. The embodiment of this invention can be of several different designs. Three are illustrated here. These designs use a SAW delay line to measure the condensate density however any IDT based acoustic delay line, oscillator, or resonator configuration as well as a mirror can be employed.

Figure 9:
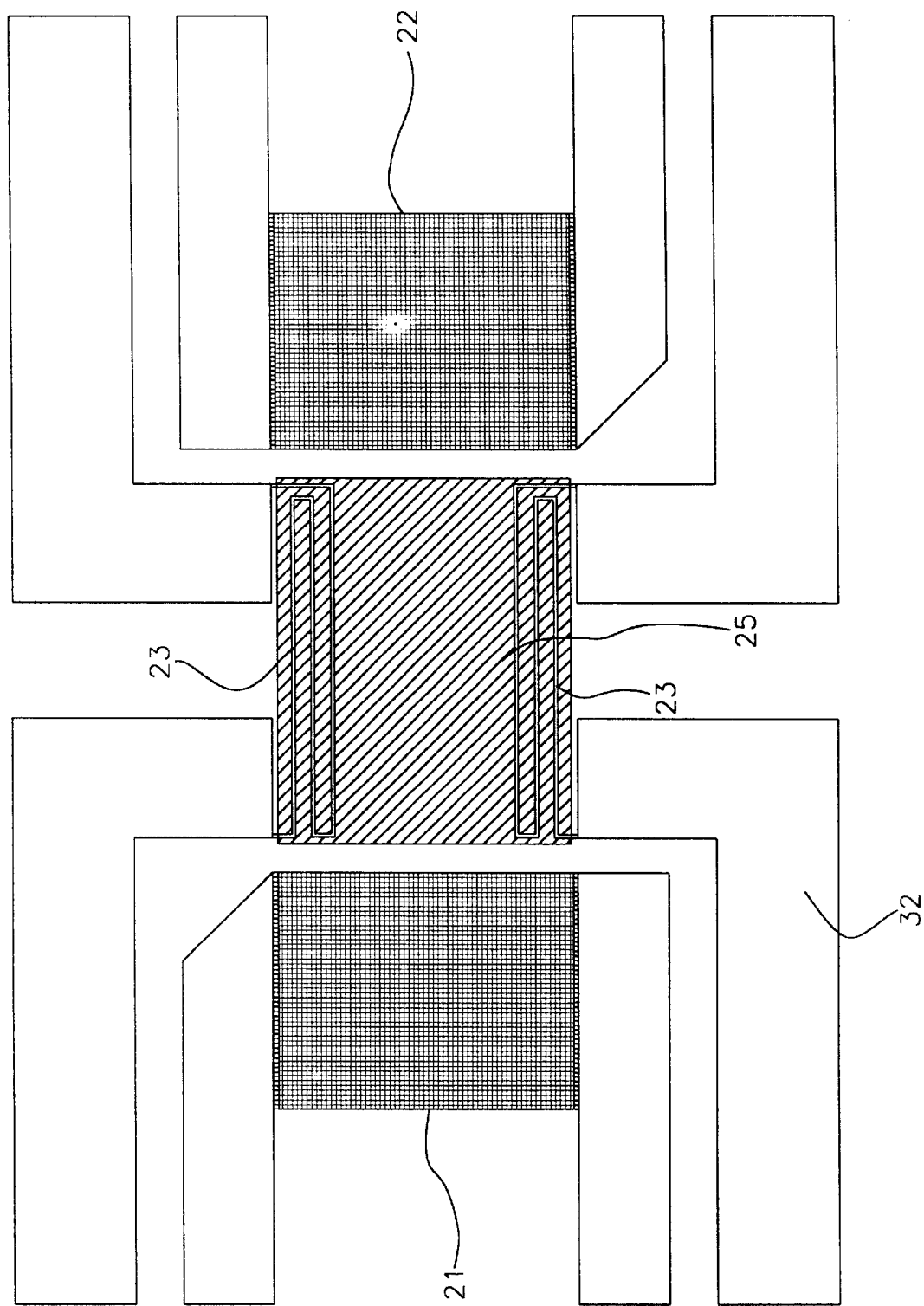
FIG. 9 is a top plan view of the embodiment shown in FIG. 8 showing the sensing film/membrane in relationship to the arrangement of the resistive integrated temperature devices relative to the sensor.

The first embodiment of this design is shown in FIG. 1. It includes a SAW delay-line channel fabricated on a piezoelectric substrate 32, consisting of input 11 and output 12 IDTs and a delay path 13 used to measure the surface density of the condensate. A second delay line channel, consisting of IDTs 14 and 15, is aligned at 90 degrees to the condensate channel and is used to measure temperature. The sensor is fabricated using standard microelectronic metallization and patterning techniques where the metal can be made of any thin fill metal such as aluminum, gold or copper. A side view of the sensor configuration showing the piezoelectric substrate 32 and the thermoelectric cooler 16 is shown in FIG. 2. For this embodiment the substrate would be ST-quartz and the condensate channel acoustic waves would propagate in the x direction. This provides a condensate channel that is relatively insensitive to temperature. Since the temperature channel is aligned at 90 degrees to the SAW channel only surface skimming bulk waves (SSBWs) will be generated due to the anisotropic nature of quartz (SAWs are not generated in this crystallographic orientation). The SSBWs pass just a few micrometers below the sensor surface and are therefore relatively insensitive to the presence of the condensate while their velocity is much more temperature sensitive than the waves of the condensate channel. This acoustic velocity therefore provides a precise measure of the surface temperature directly below the condensate. The angle between the two channels can be varied from 90 degrees as long as the active areas of the condensate and temperature channels overlap. Other piezoelectric substrate can be employed such as quartz, lithium niobate, lithium tantalite or zinc oxide. FIGS. 6 and 10 show the placement of the calibration resistive temperature devices 24 for calibrating the SSBWs by averaging the four values so as to maximize the accuracy of the SSBWs. FIGS. 9 and 10 show the surface of the sensor including a sensing film/membrane 25 that attracts the measurand.

The sensor operation is as follows: when the quartz surface is cooled to the dew (or frost) point, the resulting condensate causes a relatively large change in the SAW velocity and amplitude which allows control of the condensate surface density as described in K. A. Vetelino, P. R. Story, R. D. Mileham and D. W. Galipeau, "Improved Dewpoint Measurements Based on a SAW Sensor," Sensors and Actuators B, 35–36 (1996) 91–98, incorporated by reference herein. Since the SSBW velocity is primarily affected by temperature it can be used to measure the dew point temperature. The velocity and attenuation of the acoustic waves can be measured using one or more of several techniques that are widely used such as phase or frequency (see same reference). This technique therefore provides an acoustic detection method for condensate that is relatively insensitive to temperature while simultaneously providing an acoustic detection method for temperature that is relatively insensitive to condensate, where the acoustic waves propagate over the same physical location on the substrate. This design therefore eliminates measurement errors due to vertical or horizontal temperature gradients between the location of the condensate and the temperature sensing element that are present in all of the prior art. In addition, the measurement of temperature with acoustic waves eliminates the problem of self-heating of RTDs. The novelties of this design include: 1) the use of acoustic waves to measure both condensate and temperature and 2) the use of the appropriate acoustic waves to measure the condensate and temperature at the same location on the sensing surface.

The second embodiment of this design, shown in FIG. 3, includes a SAW delay line channel consisting of an input 17 and an output 18 IDT that can be used to measure the density of the condensate. An acoustic oscillator design (replacing the acoustic delay line in FIG. 1), consisting of IDTs 19 and 20, is aligned at 90 degrees to the condensate delay line and is used to measure temperature. For this embodiment the substrate is ST-quartz, as in the example above, with all of the same advantages. The acoustic oscillator device used to measure temperature may have advantages where high temperature resolution is desired.

The third embodiment of this design is shown in FIG. 4. The input 21 and output 22 IDTs of the delay line are separated to allow the placement of an integrated resistive temperature device (RTD) 23 in the delay path at precisely the same location as the condensate, but the integrated resistive device (RTD) 23 can also be located parallel or perpendicular to the direction of wave propagation. This design provides an alternative to the acoustic thermometers previously described, that may also provide a method for calibrating the acoustic thermometers.

A fourth embodiment of this design is shown in FIG. 5. The reflectivity of mirror 28 on the piezoelectric substrate is used to measure and control condensation using standard optical techniques, while the temperature is measured with an acoustic sensor. The input 26 and the output 27 IDTs of the acoustic sensor are separated to allow the placement of the mirror in the delay path so that the temperature is measured at precisely the same location as the condensate. Alternatively, the mirror could be eliminated and optical reflectivity of the IDT fingers and the bare substrate could be directly used to measure and control the condensate.

Measurement stability during the frost point transition and determining the state (thermodynamic phase) of the condensate. Vetelino et al., supra, have shown that the transition to frost can occur over a wide temperature range. In addition they showed that either SAW velocity or amplitude can be used to control dew density, that the complete transition to frost can be measured using SAW velocity, and that it is difficult to control frost with acoustic velocity. This part of the invention is the simultaneous use of SAW acoustic velocity and amplitude and SSBW velocity and amplitude, as feedback in a microprocessor based digital control system (reference FIG. 1 or 3) to 1) provide stable control of the condensate density whether it is dew, frost or a mix of both and 2) to specify that state of the condensate density, i.e. whether it is dew, frost or a mix of both. For example, a linear or a non-linear combination of the SAW velocity and amplitude and the SSBW velocity and amplitude may be used as feedback.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method for measuring the temperature and other properties of a chemical/biological measurand at generally the same location on a sensing surface of a sensor comprising the steps of:

subjecting the sensing surface of the surface acoustic wave sensor directly to the chemical/biological measurand;

producing a series of surface acoustic waves on the said surface of said sensor;

producing a series of surface skimming bulk waves;

propagating said surface skimming bulk waves at generally an angle to said surface acoustic waves so that accurate measurements of the temperature and other properties of the chemical/biological measurand can be made at generally the same location on the sensing device;

detecting said surface waves after transmission thereof across said surface; and measuring parameters of said detected surface waves to determine the temperature and other properties of the chemical/biological measurand at generally the same location on said surface.

2. A method as described in claim 1, wherein the said chemical/biological measurand is condensation.

3. A method as described in claim 1, wherein the said surface of said sensor includes a sensing film/membrane that attracts the measurand.

4. A method as described in claim 1, wherein the step of detecting said surface acoustic waves includes the step of detecting said acoustic waves for the purpose of measuring other properties of the chemical/biological measurand.

5. A method as described in claim 1, wherein the step of detecting said surface acoustic waves further includes the step of detecting said surface skimming bulk waves for the purpose of measuring temperature.

6. A method as described in claim 1, wherein the step of measuring parameters of said detected surface waves includes the step of measuring velocity and amplitude of both said surface acoustic waves and said surface skimming bulk waves.

7. A device for measuring the temperature and other properties of the chemical/biological measurand at generally the same location on a sensing surface of a sensor comprising:

a piezoelectric sensor having a surface directly subjected to the chemical/biological measurand;

a first acoustic device for producing a series of surface acoustic waves used for identifying properties of the chemical/biological measurand;

a second acoustic device for producing a series of surface skimming bulk waves for measuring the temperature at generally the same location as the chemical/biological measurand;

said second acoustic device being disposed such that said surface skimming bulk waves propagate across a path of said surface acoustic waves at a particular location on said sensor;

a detecting means for detecting said surface waves after transmission thereof across said surface; and a measuring means for measuring parameters of the detected surface waves to measure the temperature and other properties of the chemical/biological measurand at generally the same location as the chemical/biological measurand.

8. A device as described in claim 7, wherein said first acoustic device is at least partially opposed to said second acoustic device.

9. A device as described in claim 7, wherein at least one integrated calibration resistive temperature device is disposed at generally the same location as said acoustic device on the surface of said sensor outside the path of said surface acoustic waves.

10. A device as described in claim 7, wherein at least one integrated calibration resistive temperature device which is disposed at generally the same location as said second acoustic device on the surface of said sensor outside the path of said surface skimming bulk waves.

11. A device as described in claim 7, wherein the said chemical/biological measurand is condensation.

12. A method as described in claim 7, wherein the said surface of the sensor includes a sensing film/membrane that attracts the measurand.

13. A device as described in claim 7, wherein at least one integrated resistive temperature device is disposed at generally the same location as the chemical/biological measurand on the surface of said sensor in a path of said surface acoustic waves.

14. A device as described in claim 7, wherein at least one integrated resistive temperature device which is disposed at generally the same location as the chemical/biological measurand on the surface of said sensor not in a path of said surface acoustic waves.

15. A device as described in claim 14, wherein said at least one integrated resistive temperature device is disposed parallel to a path of said surface acoustic waves.

16. A device as described in claim 7, wherein a reflective device such as a mirror that is disposed at generally the same location as the chemical/biological measurand on the surface of said sensor for identifying the chemical/biological measurand.

17. A device as described in claim 7, wherein said piezoelectric sensor includes a thermoelectric cooler connected to a lower surface of said substrate, and a plurality of spaced heat sink members depending from a lower surface of said thermoelectric cooler.

18. A device for measuring the temperature and other properties of a chemical/biological measurand at generally the same location on a sensing surface of a sensor comprising:

a piezoelectric sensor having a surface having a sensing film/membrane that attracts the chemical/biological measurand and having a thermoelectric cooler connected to a lower surface, and having a plurality of spaced heat sink members depending from a lower surface of said thermoelectric cooler;

a wave producing means for producing surface waves on said chemical/biological measurand on said surface of said sensor, and including a first acoustic device for producing a series of surface acoustic waves for identifying density of condensation on said surface, and further including a second acoustic device for producing a series of surface skimming bulk waves for identifying the temperature at the location of the condensation, said second acoustic device being disposed relative to said sensor such that said second acoustic device sends said surface skimming bulk waves across a path of said surface acoustic waves;

a detecting means for detecting said waves after transmission thereof across said surface; and a measuring means for measuring parameters of the detected waves to at least identify the properties of the chemical/biological measurand and for measuring parameters of the temperature at generally the same location as the chemical/biological measurand.

19. A device as described in claim 18, wherein at least one integrated calibration resistive temperature device is disposed at generally the same location as said acoustic device on the surface of said sensor outside the path of said surface acoustic waves.

20. A device as described in claim 18, wherein at least one integrated calibration resistive temperature device which is disposed at generally the same location as said second acoustic device on the surface of said sensor outside the path of said surface skimming bulk waves.

\* \* \* \* \*